United States Patent
Kempers et al.

(10) Patent No.: US 9,333,262 B2
(45) Date of Patent: May 10, 2016

(54) GUERBET ALCOHOL MIXTURES AND USES THEREOF

(71) Applicant: BASF SE, Ludwigshafen (DE)

(72) Inventors: Peter Kempers, Mönchengladbach (DE); Rolf Kawa, Monheim (DE); Stefan Brüning, Düsseldorf (DE); Jadranka Milardovic, Düsseldorf (DE); Eike Ulf Mahnke, Velbert (DE); Heinz-Josef Krüppel, Grevenbroich (DE); Markus Dierker, Düsseldorf (DE); Burkhard Beckedahl, Düsseldorf (DE)

(73) Assignee: BASF SE, Ludwigshafen (DE)

( * ) Notice: Subject to any disclaimer, the term of this patent is extended or adjusted under 35 U.S.C. 154(b) by 239 days.

(21) Appl. No.: 13/768,264

(22) Filed: Feb. 15, 2013

(65) Prior Publication Data

US 2013/0217788 A1    Aug. 22, 2013

Related U.S. Application Data

(60) Provisional application No. 61/599,965, filed on Feb. 17, 2012.

(51) Int. Cl.
*A61K 47/10* (2006.01)
*A61K 8/34* (2006.01)
*A61Q 19/00* (2006.01)

(52) U.S. Cl.
CPC ............. *A61K 47/10* (2013.01); *A61K 8/345* (2013.01); *A61Q 19/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 3,553,192 | A | 1/1971 | Gauri et al. |
| 5,705,169 | A | 1/1998 | Stein et al. |
| 5,730,960 | A | 3/1998 | Stein et al. |
| 5,840,943 | A | 11/1998 | Ansmann et al. |
| 6,193,960 | B1 | 2/2001 | Metzger et al. |
| 6,919,074 | B2 | 7/2005 | Milbradt et al. |
| 7,074,395 | B2 | 7/2006 | Milbradt et al. |
| 2006/0159924 | A1 | 7/2006 | Hauser et al. |

FOREIGN PATENT DOCUMENTS

| | | |
|---|---|---|
| DE | 19712033 | 9/1998 |
| EP | 0693471 | 1/1998 |
| EP | 0694521 | 1/1998 |
| EP | 0818450 | 1/1998 |
| EP | 0766661 | 8/1999 |
| EP | 0970998 | 1/2000 |
| JP | S53-052630 | 5/1978 |
| JP | S54-088215 | 7/1979 |
| JP | 2003-012438 | 1/2003 |
| JP | 2003-502352 | 1/2003 |
| JP | 2003-063923 | 3/2003 |
| JP | 2006-504649 | 2/2006 |
| WO | WO-2007/107966 | 9/2007 |

OTHER PUBLICATIONS

Knothe, G. H.; Lipid Chemistry: Guerbet Compounds, http://lipidlibrary.aocs.org/chemistry/guerbet/index.htm, dated Dec. 22, 2011.*
Sulzbacher, M. "The Guerbet reaction of cetyl alcohol" J. Applied Chem., 1955, 5, 637-41.*
Sasol, Sasol Olefins and Surfactants, Isofol C12-C32, Defined Branched Guerbet Alcohols. http://www.sasoltechdata.com/tds/ISOFOL.pdf, commercially available prior to applicant's priority date. No date available.*
O'Lenick, A. J.; "A Review of Guerbet Chemistry" Nov. 29, 2003 http://web.archive.org/web/20031129044156/http://zenitech.com/documents/guerbet_chemistry.pdf.*
Gast, L. E. et al. "Reactions of unsaturated fatty alcohols. VI Guerbet reactions of soybean and linseed alcohols." J. of the American Oil Chemists Society, 1958, 35, 703-707.*
O'Lenick, Anthony J., et al., Guerbet Alcohols: A Versatile Hydrophobe, *Soap/Cosmetics/Chemical Specialities*, Apr. 1987, pp. 52, 54, 55, 115.

* cited by examiner

*Primary Examiner* — Mina Haghighatian
*Assistant Examiner* — Erin Hirt
(74) *Attorney, Agent, or Firm* — Servilla Whitney LLC

(57) ABSTRACT

Mixtures of Guerbet alcohols, their use in cosmetic and/or pharmaceutical preparations, and also cosmetic and/or pharmaceutical preparations comprising mixtures of Guerbet alcohols are described. Of suitability as petroleum jelly substitute are in particular Guerbet alcohol mixtures with a melting range, measured by differential scanning calorimetry (DSC), between −20° C. and +70° C., where the width of the melting range comprises at least 30 temperature degrees and the maximum of the melting range is 35±10° C. These are obtainable for example by reacting
a) 55 to 95% by weight of cetylstearyl alcohol,
b) 5 to 45% by weight of fatty alcohols with a chain length of from 8 to 22 carbon atoms and
c) optionally an aliphatic diol having at least 3 carbon atoms.

9 Claims, No Drawings

GUERBET ALCOHOL MIXTURES AND USES THEREOF

CROSS-REFERENCE TO RELATED APPLICATIONS

This application claims priority to U.S. Provisional Application No. 61/599,965, filed Feb. 17, 2012, the entire contents of which are incorporated by reference.

FIELD

Aspects of the present invention relates to mixtures of Guerbet alcohols, their use in cosmetic and/or pharmaceutical preparations as petroleum jelly substitute, and cosmetic and/or pharmaceutical preparations comprising mixtures of Guerbet alcohols.

BACKGROUND

Petroleum jelly is a tried and tested constituent of many cosmetic and/or pharmaceutical bases for topical application. It is used very widely in leave-on and rinse-off preparations, as the basis of creams and ointments and can, for example, also be used in shower baths.

Petroleum jelly belongs to the hydrocarbon gels and is a two-phase system with 70 to 90% of a liquid phase of n- and isoparaffins and olefin hydrocarbons such as cetene, heptadecene and octadecene, and also 10 to 30% of a solid phase. The solid phase consists of a microcrystalline fraction predominantly of isoparaffins and small fractions of alicycles and a crystalline fraction of n-paraffins. The gel structure of petroleum jelly arises as a result of the formation of a framework which is formed by the longer-chain solid paraffins. These position themselves—held via van der Waals-London forces—in parallel with one another and form so-called fringed micelles since the ends of the long-chain paraffins protrude unevenly from the micelle and contribute in part to the formation of further micelles. This produces a three-dimensional framework by virtue of numerous linked-together islands of parallel long-chain paraffins into which the liquid hydrocarbons are intercalated. The corresponding composition of crystalline, microcrystalline regions and liquid hydrocarbons determines the formation of this gel structure and thus the particular rheological properties (plasticity, ductility) of petroleum jelly.

Petroleum jelly is characterized by a very wide melting range from ca. −10 to +60° C. and behaves largely neutrally in chemical terms.

Predominantly, naturally obtained petroleum jelly is used in cosmetic and pharmaceutical preparations; this is a mixture of n-paraffins, isoparaffins and hydroaromatic hydrocarbons that is produced in the residue during the refining of petroleum and which is purified by treating with concentrated sulfuric acid and bleaching earths and/or activated carbon. Different grades of petroleum jelly are produced depending on the type of purification. However, there likewise also exists a synthetically produced petroleum jelly which is obtained by dissolving paraffin and ceresin in liquid paraffin.

However, it is known that paraffins can accummulate, depending on chain length, in the liver, lymph nodes and kidneys. Time and again, it is discussed how mineral oils, being fats that are difficult to degrade, lead to an accumulation in the body and, as a result of closing the skin pores, impair the breathing of the skin or promote the development of acne. Lip care sticks containing mineral oils have therefore also already been criticized.

Despite the known good topical compatibility of paraffins, there is a continuing interest in preparations which comprise ointment bases which are characterized by production from renewable raw materials. In terms of properties, they should correspond to those of petroleum jelly. Bases hitherto for replacing petroleum jelly have relatively narrow melting ranges, and therefore the search was for possible substitute bases with a comparable broad melting range.

Even some years ago, the mixture of beeswax and plant oil served as petroleum jelly substitute. However, beeswax, being a natural product, cannot in the short term be produced in large amounts.

The international application WO 2007/107966 discloses deodorant preparations which comprise hydrogenated castor oil as petroleum jelly substitute, which is lowered in its viscosity by castor seed oil, liquid fatty alcohols and plant oils. It is assumed that fragrances remain for longer in these cosmetic bases compared with in the petroleum jelly-based preparations on account of the higher polarity of hydrogenated castor oil.

The chemical synthesis of branched-chain alcohols via the Guerbet reaction is a long-established process in the chemical industry.

The condensation of primary alcohols can be catalyzed e.g. by bases; α-branched alcohols are formed as reaction product.

There are various Guerbet alcohols on the market, e.g. Eutanol G/G16 (C16-C20 Guerbets) from BASF Personal Care and Nutrition GmbH. Sasol has various Isofol® grades on the market (e.g. Isofol® C12 to C32).

Exxon has various Exxal™ C16 to C26 grades on the market, and Jarchem Industries supplies e.g. the Jarcol™ C12 to C36 grades. Evonik Goldschmidt GmbH supplies e.g. Tegosoft® G 20.

Some short-chain Guerbet alcohol grades with a chain length of less than 20 carbon atoms are liquid at room temperature. They can be used for example as cosmetic emollients. Long-chain C32-C36-Guerbets are solid and have a high melting point in the range above 45° C. High-melting compounds generally have a clearly defined melting point and are therefore not suitable as petroleum jelly substitute. In general, the melting point of branched-chain Guerbet alcohols is significantly lower than the melting point of the corresponding linear alcohols. [Sasol Olefins & Surfactants, ISOFOL® C12-C32 Defined Branched Guerbet Alcohols, Sasol Germany GmbH, Paul Baumann Straβe 1, 45764 Marl, Germany]

SUMMARY

One aspect of the invention relates to a Guerbet alcohol mixture. The Guerget alcohol mixture has a melting range of between between −20° C. and +70° C. as measured by differential scanning calorimetry (DSC), wherein the width of the melting range is at least 30 temperature degrees and the maximum of the melting range is 35±15° C. In one or more embodiments, the Guerbet alcohol mixture has a melting range is between −10° C. and +60° C., and the width is at least 40 temperature degrees and the maximum of the melting range is 35±10° C.

Another aspect of the invention relates to a Guerbet alcohol mixture obtainable by reacting:
 a) 55 to 95% by weight of cetylstearyl alcohol; with
 b) 5 to 45% by weight of fatty alcohols with a chain length of 8 to 22 carbon atoms; and
 c) optionally 5% by weight of an aliphatic diol having at least 3 carbon atoms, with the proviso that the mixture has a melting range, measured by differential scanning calorimetry (DSC), between −20° C. and +70° C., where the width of the melting range comprises at least 30 temperature degrees and the maximum of the melting range is 35±15° C.

In one or more embodiments, the Guerbet alcohol mixture is obtainable by reacting:
a) 60 to 70% by weight of cetylstearyl alcohol;
b) 30 to 40% by weight of fatty alcohols with a chain length of from 8 to 22 carbon atoms; and
c) optionally 5% by weight of an aliphatic diol having at least 3 carbon atoms,
with the proviso that the mixture has a melting range, measured by differential scanning calorimetry, between −20° C. and +70° C., where the width of the melting range comprises at least 30 temperature degrees and the maximum of the melting range is 35±15° C.

In some embodiments, the Guerbet alcohol mixture has a melting range between −10° C. and +60° C., where the width of the melting range comprises at least 40 temperature degrees and the maximum of the melting range is 35±10° C. In one or more embodiments, the component a) consists of unbranched fatty alcohols with a chain distribution of
C16 of 45-55%, and
C18 of 45-55%.

In some embodiments, the component b) consists essentially of fatty alcohols with a chain length of from 12 to 18 carbon atoms. In one or more embodiments, the component b) consists of unbranched, saturated fatty alcohols having the following chain distribution:
C12 from 48-58% by weight
C14 from 18-24% by weight
C16 from 8-12% by weight
C18 from 11-15% by weight.

In one or more embodiments, comoponent c) comprises hexanediol. In some embodiments, the Guerbet reaction is carried out at temperatures of from 200 to 260° C. In one or more embodiments, the Guerbet reaction is operated until 60-80% of the conversion of the starting alcohols has been achieved. In some embodiments, the Guerbet alcohol mixture is obtainable by reacting:
a) 55 to 95% by weight of cetylstearyl alcohol; with
b) 5 to 45% by weight of fatty alcohols with a chain length of 8 to 22 carbon atoms; and
c) 5% by weight of an aliphatic diol having at least 3 carbon atoms,
with the proviso that the mixture has a melting range, measured by differential scanning calorimetry (DSC), between −20° C. and +70° C., where the width of the melting range comprises at least 30 temperature degrees and the maximum of the melting range is 35±15° C.

Another aspect of the invention relates to a cosmetic and/or pharmaceutical preparation comprising any of the Guerbet alcohol mixtures described above.

DETAILED DESCRIPTION

A mixture of Guerbet alcohols is described which is comparable with petroleum jelly in terms of sensorics and application properties. As used herein, "petroleum jelly," also known as "petrolatum," "white petrolatum," "soft paraffin" and "multi-hydrocarbon," refers to a semi-solid mixture of hydrocarbons. It is available, for example, under the trade name Vaseline®.

The product properties of the Guerbet alcohol mixture can be adjusted in a targeted manner through optimization of the fatty alcohol composition, selection of the fatty alcohol chain length, implementation of the Guerbet reaction and optionally the additional use of diols as crosslinkers, meaning that the mixture is comparable with the application properties and sensorics of petroleum jelly and has a comparable melting range with a similar maximum.

Data for the melting range of petroleum jelly in the literature are between 35 and 60° C. The melting range varies depending on the fraction of the crystalline areas.

However, thermal analysis by means of differential scanning calorimetry (DSC) can be used to measure the start of melting even at relatively low temperatures.

The fact that the maximum of the melting range for petroleum jelly is in the region of skin temperature and petroleum jelly is characterized by a relatively broad melting range with a slow increase from −20° C.±5° C. to 70° C.±5° C. has a substantial influence on the characteristic sensory properties of petroleum jelly.

The Guerbet alcohol mixture which has a melting behavior corresponding to petroleum jelly has therefore been selected.

Characterization of the Melting Range:

Differential scanning calorimetry (DSC) measures changes in heat flow which arise due to temperature- and time-dependent changes in the physical and chemical structure of the sample material. DSC ascertains the heat absorption of the sample material for the melting of the sample at a uniformly increasing heating rate.

Determining the change in the amount of heat can be measured in different ways. With modern DSC (differential scanning calorimetry), a distinction is made between heat-flow differential scanning calorimetry and power-compensated differential scanning calorimetry.

For measurements according to heat-flow differential scanning calorimetry (tables 1a and b), the heat-flow DSC Q100 from TA Instruments (Waters GmbH) was used.

In each case, five to ten milligrams of the sample material were weighed into small aluminum pans and hermetically encapsulated (cold-sealed). These pans were subjected to a temperature program of −80° C. to +100° C. at a heating rate of 5 K/min and the melting behavior and/or crystallization behavior was analyzed. The results were measured reproducibly.

Evaluation of samples with a non-constant baseline (on account of the temperature dependency of the heat capacity of the mixtures) and a very wide melting range is subject to considerable variations with customary optical means by reading off the values from the diagrams obtained, meaning that the temperature values have been established by reference to enthalpy values.

A linear peak evaluation from −60° C. to the end of melting (lay between +40° C. and +80° C.) was carried out. The enthalpy calculated in this way was viewed percentually. Consequently, melting ranges can be indicated by choosing the temperature at 5% of the total melt enthalpy as starting point and at 99% of the total melt enthalpy as the end of the range (table 1a). This selection corresponded to the values visually ascertained approximately from the diagram.

The temperature maximum ascertained was the temperature value which arose for the maximum peak. This could be read off with adequate precision from the diagrams (table 1b—right-hand column).

TABLE 1a

Enthalpy - Temperature trace of the DSC measurement

| | E in J/g total | T (α) in ° C. | T (Ω) in ° C. | 1% E in J/g | 1% T in ° C. | 5% E in J/g | 5% T in ° C. | 10% E in J/g | 10% T in ° C. | 50% E in J/g | 50% T in ° C. | 90% E in J/g | 90% T in ° C. | 95% E in J/g | 95% T in ° C. | 99% E in J/g | 99% T in ° C. |
|---|---|---|---|---|---|---|---|---|---|---|---|---|---|---|---|---|---|
| Petroleum jelly Enzborn | 64 | −60 | 76 | 1 | −48 | 3 | −32 | 6 | −17 | 32 | 26 | 57 | 50 | 61 | 56 | 63 | 67 |
| Petroleum jelly Sigma Aldrich | 63 | −60 | 76 | 1 | −49 | 3 | −30 | 6 | −13 | 32 | 29 | 57 | 54 | 60 | 59 | 63 | 67 |
| Petroleum jelly Hansen | 73 | −60 | 76 | 1 | −44 | 3 | −18 | 7 | −5 | 37 | 22 | 66 | 46 | 70 | 55 | 73 | 67 |
| Petroleum jelly VWR Prolabo | 90 | −60 | 75 | 1 | −38 | 4 | −10 | 9 | 0 | 45 | 24 | 81 | 47 | 85 | 56 | 89 | 67 |
| A 70-30 | 117 | −60 | 67 | 1 | −36 | 6 | −6 | 12 | 3 | 59 | 19 | 105 | 31 | 111 | 41 | 116 | 60 |
| B 60-35 | 111 | −60 | 38 | 1 | −31 | 6 | −10 | 11 | 3 | 56 | 19 | 100 | 30 | 106 | 31 | 110 | 32 |
| C 60-40 | 125 | −60 | 56 | 1 | −18 | 6 | −5 | 12 | −1 | 62 | 27 | 112 | 41 | 119 | 42 | 124 | 44 |
| D 95-5 Ocenol | 134 | −60 | 59 | 1 | 13 | 7 | 18 | 13 | 21 | 67 | 44 | 121 | 51 | 127 | 52 | 133 | 53 |
| E 62.5-32.5-5 | 115 | −60 | 52 | 1 | −19 | 6 | −4 | 12 | 1 | 58 | 22 | 104 | 36 | 109 | 37 | 114 | 39 |

TABLE 1b

Melting ranges of prepared Guerbet alcohol mixtures

| | Guerbet alcohol mixture and comparison | Weight ratio | Melting range ° C. | Melting range maximum ° C. |
|---|---|---|---|---|
| A | Lanette O/Lorol | 70:30 | −6-60 | 30 |
| B | Lanette O/Lorol | 65:35 | −10-32 | 30 |
| C | Lanette O/Lorol | 60:40 | −5-44 | 40 |
| D | Lanette O/Ocenol 50/55 | 95:5 | 18-53 | 50 |
| E | Lanette O/Lorol/ hexanediol | 62.5:32.5:5 | −4-39 | 34 |
| White Petroleum jelly | 4 different grades: Source: Sigma Aldrich/Hansen/ Enzborn/VWR Prolabo | | −22-70 | 45 (Sigma) 35 (Enzborn) 25 (Prolabo) 26 (Hansen) |

Aspects of the invention provide Guerbet alcohol mixtures with a melting range, measured by differentical scanning calorimetry (DSC), between −20° C. and +70° C., where the width of the melting range comprises at least 30 temperature degrees and the maximum of the melting range is 35±15° C. As a result of fluctuations in the composition of petroleum jelly, especially the different fractions of crystalline areas, the values ascertained using the precise method of DSC vary, meaning that the melting range ascertained for the Guerbet alcohol mixtures according to one or more embodiments of the invention is also in the temperature range between −20° C. and +70° C., specifically between −15° C. and +65° C., particularly specifically between −10° C. and +60° C. and specifically between −10° C. and 55° C.

In this connection, the melting range does not have to span the entire width, but it should cover at least a range of 30 temperature degrees (° C.) within the temperature range between −20° C. and +70° C., specifically in the temperature range between −15° C. and +65° C., more specifically within the temperature range between −10° C. and +60° C. and specifically within the temperature range between −10° C. and 55° C., and in certain embodiments, comprise at least 40 temperature degrees (° C.) in its width. The maximum of the melting range here is 35±15° C., specifically 35±10° C. and more specifically 35±5° C., it thus falls approximately within the skin temperature range.

One or more embodiments therefore relate to Guerbet alcohol mixtures with a melting range between −15° C. and +65° C., a width of the melting range of at least 40 temperature degrees and a maximum at 35±10° C.

Some embodiments relate to to Guerbet alcohol mixtures with a melting range between −10° C. and +60° C., a width of the melting range of at least 40 temperature degrees and a maximum at 35±10° C., and specifically Guerbet alcohol mixtures with a melting range between −15° C. and +55° C., a width of the melting range of at least 40 temperature degrees and a maximum at 35±5° C.

Surprisingly, it has been found that Guerbet alcohol mixtures which have a melting range, measured by differential scanning calorimetry (DSC), between −20° C. and +70° C., where the width of the melting range comprises at least 30 temperature degrees and the maximum of the melting range is 35±15° C., are obtainable by reacting
  a) 45 to 95% by weight of cetylstearyl alcohol,
  b) 5 to 55% by weight of fatty alcohols with a chain length of from 8 to 22 carbon atoms and
  c) optionally 5% by weight of an aliphatic diol having at least 3 carbon atoms.

Some embodiments relate to Guerbet alcohol mixtures which are obtainable by reacting
  a) 60 to 70% by weight of cetylstearyl alcohol,
  b) 30 to 40% by weight of fatty alcohols with a chain length of from 8 to 22 carbon atoms and c) optionally 5% by weight of an aliphatic diol having at least 3 carbon atoms, with the proviso that the mixture has a melting range, measured by differential scanning calorimetry (DSC), between −20° C. and +70° C., where the width of the melting range comprises at least 30 temperature degrees and the maximum of the melting range is 35±15° C., more specifically with the proviso that the melting range is between −10° C. and +60° C., comprises a width of at least 40 temperature degrees and the maximum of the melting range is 35±10° C.

The component a) cetylstearyl alcohol is a mixture of the long-chain fatty alcohols hexadecan-1-ol (C16) and octadecan-1-ol (C18), which is used as nonionic coemulsifier, emollient and consistency regulator in the cosmetic and pharmaceutical sector. A composition of cetyl alcohol and stearyl alcohol having the following chain distribution is commercially available under the name Lanette® O and is suitable particularly for producing the preparation according to the invention:

C16 of 45-55% by weight and
C18 of 45-55% by weight.

Cetylstearyl alcohol has a melting range from 48-53° C. and is biodegradable. The fatty alcohols used for producing the Guerbet alcohol mixture have a chain length of from 8 to 22 carbon atoms and can be saturated or unsaturated.

A suitable unsaturated fatty alcohol is, for example, oleyl alcohol (Ocenol 50/55) which, with cetylstearyl alcohol in the weight ratio 5:95, has a melting range from 15 to 50° C.

In one or more embodiments, unbranched, saturated fatty alcohols having 12 to 20 carbon atoms are used. In order to correspond as far as possible to the properties of petroleum jelly, a chain distribution of unbranched fatty alcohols which has proven particularly useful is as follows:

C12-alcohol from 48-58% by weight
C14-alcohol from 18-24% by weight
C16-alcohol from 8-12% by weight
C18-alcohol from 11-15% by weight.

Component c) can be used in order to further crosslink the alcohols with one another. This crosslinking allows further control and adjustment of the desired melting range.

The aliphatic diols should have at least 3 carbon atoms, with certain embodiments related to to using hexanediol, and more specifically hexane-1,6-diol.

Synthesis Conditions for Guerbet Reactions:

In one or more embodiments, the Guerbet reactions are carried out in the temperature range from 200 to 260° C., further embodiments relating to a temperature range from 220 to 250° C.

A catalytic amount of base, for example potassium hydroxide solution, can be added to the alcohols to be Guerbetized. Optionally, in addition, co-catalysts such as zinc oxide or transition metals or compounds thereof are also used.

The chain length of the fatty alcohols can be varied widely here and it is also possible to Guerbetize mixtures of different alcohols together. The starting alcohols used are natural fatty alcohols with a carbon chain length of from 8 to 22 carbon atoms. Under specific conditions, such as increased pressure or selection of suitable catalysts, it is also possible to use shorter-chain starting alcohols. The use of unsaturated alcohols is likewise possible.

By adding diols, it is possible to partially crosslink the resulting Guerbet alcohols and to thus establish a wider molecular weight distribution having the physical properties resulting therefrom. In this connection, it is possible to use diols having at least 3 carbon atoms, specifically 3 to 18 carbon atoms, and further embodiments relate to using hexanediol. The use of polyols such as, for example, trimethylolpropane, is also possible.

The Guerbet reaction is specifically operated to a conversion of the starting alcohols of 60-80%. Depending on the desired profile of properties, the remaining starting alcohols can then remain in the product or else be distilled off.

In the crude Guerbet alcohols, the remaining catalyst base is neutralized with a strong acid, and salts are removed by washing with water. Finally, the pH can be lowered to the desired, skin-neutral range using a suitable acid such as lactic acid.

On account of the physical, chemical and in particular rheological properties, the mixtures of Guerbet alcohols can be used to replace petroleum jelly in cosmetic or pharmaceutical preparations.

The Guerbet alcohol mixtures according to one or more embodiments of the invention have a comparable melting range to petroleum jelly, exhibit comparable sensory properties to petroleum jelly, but nevertheless have better application properties in surface-active systems since the amount of foam in formulations with Guerbet alcohols mixtures is greater than in petroleum jelly-containing preparations.

Cosmetic Preparations

The preparations according to one or more embodiments of the invention according to one or more embodiments of the invention are suitable as a basis in all pharmaceutical preparations for topical application and all cosmetic compositions for body care and cleaning, such as e.g. body oil, baby oil, body milk, creams, lotions, sprayable emulsions, sun protection compositions and antiperspirants. They can be used particularly in surfactant-containing preparations such as e.g. liquid soaps and bar soaps, foam and shower baths, hair shampoos and hair rinses. Also possible is use as care component on tissues, papers, wipes, nonwoven products, sponges, puffs, plasters and bandages which are widespread in the hygiene and care sector (wet wipes for baby hygiene and baby care, cleansing wipes, face cleansing wipes, skincare wipes, care wipes with active ingredients to combat skin aging, wipes with sun protection formulations and insect repellants, and also wipes for decorative cosmetics or for after-sun treatment, toilet wet wipes, antiperspirant wipes, diapers, pocket tissues, wet wipes, hygiene products, self-tanning wipes). They can also be used inter alia in preparations for hair care, hair cleaning or hair coloring. They can furthermore be used in preparations of decorative cosmetics, such as, for example, lipsticks, lip gloss, make-up, foundations, powders, eye shadows, mascara and the like.

The use concentrations in the respective formulations and preparations correspond to those of petroleum jelly. The pharmaceutical and cosmetic preparations comprising the Guerbet alcohol mixtures according to one or more embodiments of the invention according to one or more embodiments of the invention are therefore likewise provided by the invention. Since the Guerbet alcohol mixtures, especially in surface-active preparations, have advantages over using petroleum jelly by virtue of the fact that the amount of foam is greater than in comparable petroleum jelly-containing systems, cosmetic and/or pharmaceutical preparations comprising the Guerbet alcohol mixtures according to one or more embodiments of the invention according to one or more embodiments of the invention and interface-active substances are also provided by the invention.

Depending on the application purpose, the cosmetic formulations may comprise a series of further auxiliaries and additives, such as, for example, surfactants, further oil bodies, emulsifiers, pearlescent waxes, consistency regulators, thickeners, superfatting agents, stabilizers, polymers, fats, waxes, lecithins, phospholipids, biogenic active ingredients, UV light protection factors, antioxidants, deodorants, antiperspirants, antidandruff agents, film formers, swelling agents, insect repellants, self-tanning agents, tyrosinase inhibitors (depigmentation agents), fillers, hydrotropes, solubilizers, preservatives, perfume oils, dyes etc., which are listed below by way of example.

Interface-Active Substance b-1)

In one embodiment of the invention, the preparations according to one or more embodiments of the invention comprise at least one interface-active substance. The preparations according to one or more embodiments of the invention comprise the interface-active substance(s) in an amount of from 0 to 80% by weight, in particular 0 to 40% by weight, specifically 0.1 to 20% by weight, or more specifically 0.1 to 15% by weight and in particular 0.1 to 10% by weight, based on the total weight of the preparation.

Suitable interface-active substances are in principle any substance which lowers the surface tension between the aqueous and nonaqueous phases. Interface-active substances comprise emulsifiers and surfactants.

In one embodiment of the invention, the preparation according to one or more embodiments of the invention comprises more than one interface-active substance. The person skilled in the art uses customary systems (e.g. emulsifier and co-emulsifier) depending on the other components.

A suitable emulsifier is in principle any interface-active substance, but in particular substances with an HLB value of from 1 to 20 according to the Griffin scale. Every emulsifier is assigned a so-called HLB value (a dimensionless value between 1 and 20, Griffin scale) which indicates whether preferred solubility in water or oil is present. Numbers below 9 indicate preferentially oil-soluble, hydrophobic emulsifiers; numbers above 11 water-soluble, hydrophilic emulsifiers. The HLB value says something about the equilibrium of the size and strength of the hydrophilic and the lipophilic groups of an emulsifier.

The solubility of the emulsifier in the two phases in practice determines the type of emulsion. If the emulsifier is more soluble in water, then a O/W emulsion is obtained. If, on the other hand, the emulsifier has a better solubility in the oil phase, a W/O emulsion is formed under otherwise identical preparation conditions.

Nonionic Emulsifiers

The group of nonionic emulsifiers includes, for example:
(1) Addition products of from 2 to 50 mol of ethylene oxide and/or 1 to 20 mol of propylene oxide onto linear fatty alcohols having 8 to 40 carbon atoms, onto fatty acids having 12 to 40 carbon atoms and onto alkylphenols having 8 to 15 carbon atoms in the alkyl group.
(2) $C_{12}$-$C_{18}$-Fatty acid mono- and diesters of addition products of from 1 to 50 mol of ethylene oxide onto glycerol.
(3) Sorbitan mono- and diesters of saturated and unsaturated fatty acids having 6 to 22 carbon atoms and ethylene oxide addition products thereof.
(4) Alkyl mono- and oligoglycosides having 8 to 22 carbon atoms in the alkyl radical and ethoxylated analogs thereof.
(5) Addition products of from 7 to 60 mol of ethylene oxide onto castor oil and/or hydrogenated castor oil.
(6) Polyol and in particular polyglycerol esters, such as e.g. polyol poly-12-hydroxystearates, polyglycerol polyricinoleate, polyglyceryl-4 laurates, polyglycerol diisostearate or polyglycerol dimerate. Likewise of suitability are mixtures of compounds of two or more of these substances classes, such as e.g. polyglyceryl-4 diisostearates/polyhydroxystearates/sebacates.
(7) Addition products of from 2 to 15 mol of ethylene oxide onto castor oil and/or hydrogenated castor oil.
(8) Partial esters based on linear, branched, unsaturated or saturated $C_6$-$C_{22}$-fatty acids, ricinoleic acid and 12-hydroxystearic acid and polyglycerol, pentaerythritol, dipenta-erythritol, sugar alcohols (e.g. sorbitol), alkyl glucosides (e.g. methylglucoside, butylglucoside, laurylglucoside), and polyglucosides (e.g. cellulose), or mixed esters, and also sucrose polystearates (commercially available as Emulgade® SUCRO, Cognis GmbH).
(9) Polysiloxane-polyalkyl-polyether copolymers and corresponding derivatives.
(10) Mixed esters of pentaerythritol, fatty acids, citric acid and fatty alcohol and/or mixed esters of fatty acids having 6 to 22 carbon atoms, methylglucose and polyols, specifically glycerol or polyglycerol.

The addition products of ethylene oxide and/or of propylene oxide onto fatty alcohols, fatty acids, alkylphenols, glycerol mono- and diesters, and also sorbitan mono- and diesters of fatty acids or onto castor oil are known, commercially available products. These are homolog mixtures, the average degree of alkoxylation of which corresponds to the ratio of the quantitative amounts of ethylene oxide and/or propylene oxide and substrate with which the addition reaction is carried out. They are W/O or O/W emulsifiers depending on the degree of ethoxylation. $C_{12/18}$-Fatty acid mono- and diesters of addition products of ethylene oxide onto glycerol are known as refatting agents for cosmetic preparations.

Particularly well-suited and mild emulsifiers according to one or more embodiments of the invention are polyol poly-12-hydroxystearates and mixtures thereof, which are sold for example under the names "Dehymuls® PGPH" (W/O emulsifier) or "Eumulgin® VL 75" (mixture with cocoglucosides in the weight ratio 1:1, O/W emulsifier) or Dehymuls® SBL (W/O emulsifier) from Cognis Deutschland GmbH. In this connection, reference may be made in particular to the European patent EP 766 661 B1. The polyol component of these emulsifiers can be derived from substances which have at least two, specifically 3 to 12 and in particular 3 to 8, hydroxyl groups and 2 to 12 carbon atoms.

Suitable lipophilic W/O emulsifiers are in principle emulsifiers with an HLB value of 1 to 8, which are summarized in numerous tabular works and are known to the person skilled in the art. For ethoxylated products, the HLB value can also be calculated according to the following formula: HLB=(100−L): 5, where L is the weight fraction of the lipophilic groups, i.e. of the fatty alkyl or fatty acyl groups in percent by weight in the ethylene oxide adducts.

From the group of W/O emulsifiers, partial esters of polyols, in particular of $C_4$-$C_6$-polyols, are particularly advantageous, such as, for example, partial esters of pentaerythritol or sugar esters, e.g. sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Suitable emulsifiers are also addition products of 1 to 30, specifically 5 to 10, mol of ethylene oxide onto the specified sorbitan esters.

Depending on the formulation, it may be advantageous to additionally use at least one emulsifier from the group of nonionic O/W emulsifiers (HLB value: 8-18) and/or solubilizers. These are, for example, the ethylene oxide adducts already mentioned in the introduction and having a correspondingly high degree of ethoxylation, e.g. 10-20 ethylene oxide units for O/W emulsifiers and 20-40 ethylene oxide units for so-called solubilizers. According to one or more embodiments of the invention, ceteareth-12, ceteareth-20 and PEG-20 stearate are particularly advantageous as O/W emulsifiers. Suitable solubilizers are specifically Eumulgin® HRE 40 (INCI: PEG-40 hydrogenated castor oil), Eumulgin® HRE 60 (INCI: PEG-60 hydrogenated castor oil), Eumulgin® L (INCI: PPG-1-PEG-9 lauryl glycol ether), and Eumulgin® SML 20 (INCI: Polysorbate-20).

Nonionic emulsifiers from the group of alkyl oligoglycosides are particularly skin-friendly and therefore specifically suitable as O/W emulsifiers. $C_8$-$C_{22}$-Alkyl mono- and oligoglycosides, their preparation and their use are known from the prior art. Their preparation takes place in particular by reacting glucose or oligosaccharides with primary alcohols having 6 to 24, specifically 8 to 22, carbon atoms. As regards the glycoside radical, it is the case that both monoglycosides, in which one cyclic sugar radical is glycosidically bonded to the fatty alcohol, and also oligomeric glycosides with a degree of oligomerization up to specifically about 8 are suitable. The degree of oligomerization here is a statistical average value based on a homolog distribution customary for such technical products. Products which are available under the name Plantacare® or Plantaren® comprise a glucosidically bonded $C_8$-$C_{16}$-alkyl group on an oligoglucoside radical, the average degree of oligomerization of which is 1 to 2. The acylglucamides derived from glucamine are also suitable as nonionic emulsifiers.

According to some embodiments of the invention, preference is given to a product which is sold under the name Emulgade® PL 68/50 by Cognis Deutschland GmbH and is a 1:1 mixture of alkyl polyglucosides and fatty alcohols. According to one or more embodiments of the invention, it is advantageously also possible to use a mixture of lauryl glucoside, polyglyceryl-2 dipolyhydroxystearate, glycerol and water, which is commercially available under the name Eumulgin® VL 75.

Suitable emulsifiers are also substances such as lecithins and phospholipids. Examples of natural lecithins which may be mentioned are the kephalins, which are also referred to as phosphatidic acids and are derivatives of 1,2-diacyl-sn-glycerol-3-phosphoric acids. By contrast, phospholipids are usually understood as meaning mono- and specifically diesters of phosphoric acid with glycerol (glycerol phosphates) which are generally included with the fats. In addition, sphingosines and/or sphingolipids are also suitable.

Silicone emulsifiers, for example, may be present as emulsifiers. These can be selected for example from the group of alkylmethicone copolyols and/or alkyldimethicone copolyols, in particular from the group of compounds which are characterized by the following chemical structure:

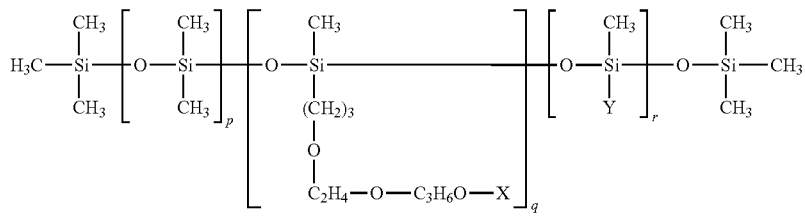

in which X and Y, independently of one another, are selected from the group H (hydrogen), and the branched and unbranched alkyl groups, acyl groups and alkoxy groups having 1-24 carbon atoms, p is a number from 0-200, q is a number from 1-40, and r is a number from 1-100.

One example of silicone emulsifiers to be used particularly advantageously within the context of the present invention are dimethicone copolyols, which are sold by Evonik Goldschmidt under the trade names AXIL® B 8842, ABIL® B 8843, ABIL® B 8847, ABIL® B 8851, ABIL® B 8852, ABIL® B 8863, ABIL® B 8873 and ABIL® B 88183.

A further example of interface-active substances to be used particularly advantageously within the context of the present invention is cetyl PEG/PPG-10/1 dimethicone (cetyl dimethicone copolyol), which is sold by Evonik Goldschmidt under the trade name ABIL® EM 90.

A further example of interface-active substances to be used particularly advantageously within the context of the present invention is the cyclomethiconedimethicone copolyol, which is sold by Evonik Goldschmidt under the trade name ABIL® EM 97 and ABIL® WE 09.

Furthermore, the emulsifier lauryl PEG/PPG-18/18 methicone (laurylmethicone copolyol) has proven to be very particularly advantageous and is available under the trade name Dow Corning® 5200 Formulation Aid from Dow Corning Ltd. Also advantageous is a silicone emulsifier with the INCI name Cyclopentasiloxane and PEG/PG-18-18 Dimethicone, which is available for example under the trade name Dow Corning® 5225 C Formulation Aid.

A further advantageous silicone emulsifier is octyl dimethicone ethoxyglucoside from Wacker. For a water-in-silicone oil emulsion according to the invention, all known emulsifiers used for this type of emulsion can be used. In some embodiments, twater-in-silicone emulsifiers include cetyl PEG/PPG-10/1 dimethicone and lauryl PEG/PPG-18/18 methicone [e.g. ABIL® EM 90 Evonik Goldschmidt), DC5200 Formulation Aid (Dow Corning)], and any desired mixtures of both emulsifiers.

A suitable anionic O/W emulsifier is e.g. the product available under the INCI name Disodium Cetearyl Sulfosuccinate (trade name Eumulgin® Prisma, Cognis GmbH).

Surfactants

In one embodiment of the invention, the preparations according to one or more embodiments of the invention comprise at least one surfactant as interface-active compounds. Interface-active substances which may be present are anionic, nonionic, cationic and/or amphoteric or zwitterionic surfactants. In surfactant-containing cosmetic preparations, such as, for example, shower gels, foam baths, shampoos etc., and in some embodiments, at least one anionic surfactant is present.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolyzates (in particular wheat-based plant products), polyol fatty acid esters, sugar esters, sorbitan esters, polysorbates and amine oxides. If the nonionic surfactants comprise polyglycol ether chains, these can have a conventional homolog distribution, but in some embodiments, have a narrowed homolog distribution.

Zwitterionic surfactants is the term used to refer to those surface-active compounds which carry at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxylmethyl-3-hydroxyethyl-imidazoline having in each case 8 to 18 carbon atoms in the alkyl or acyl group, and also cocoacylaminoethylhydroxyethyl carboxymethylglycinate. In one or more embodiments, the zwitterionic surfactant is the fatty acid amide derivative known under the INCI name Cocamidopropyl Betaine.

Likewise suitable, especially as co-surfactants, are ampholytic surfactants. Ampholytic surfactants are understood as meaning those surface-active compounds which, apart from a C$_8$-C$_{18}$-alkyl or acyl group in the molecule, comprise at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids (commercially available for example under the trade name Dehyton® DC), N-hydroxyethyl N-alkylamidopropylglycines, N-alkyltaurines, N-alklylsarcosines, 2-alkylaminopropionic acids and alkylaminoacetic acids having in each case about 8 to 18 carbon atoms in the alkyl group. In some emboediments, the ampholytic surfactants comprise N-cocoalkylaminopropionate, cocoacylaminoethylaminopropionate and C$_{12-18}$-acylsarcosine. Also suitable are derivatives of N-alkyliminodipropionic acids, such as, for example, N-lauryl-beta-iminopropionates, commercially available under the trade name Deriphat® 160 C. Also suitable are amphoacetates, such as e.g. cocoamphoacetates (e.g. Dehyton® MC) or cocoamphodiacetates (e.g. Dehyton® DC).

Anionic surfactants are characterized by a water-solubilizing, anionic group such as e.g. a carboxylate, sulfate, sulfonate, citrate or phosphate group and a lipophilic radical. Skin-compatible anionic surfactants are known in large numbers to the person skilled in the art from relevant handbooks and are commercially available. These are in particular alkylsulfates in the form of their alkali metal, ammonium or alkanolammonium salts, alkyl ether sulfates, alkyl ether carboxylates, acyl isethionates, acyl sarcosinates, acyltaurines with linear alkyl or acyl groups having 12 to 18 carbon atoms, and sulfosuccinates and acylglutamates in the form of their alkali metal or ammonium salts. Particularly suitable anionic surfactants are glyceryl stearate Citrate (such as e.g. commercially available under the trade names Imwitor® 370, Imwitor® 372P, Axol® C, 62 or Dracorin® CE 614035) or glycerol stearate lactate compounds. An example of a suitable alkylsulfate is sodium cetearyl sulfate (trade name Lanette® E), an example of a suitable phosphate is potassium cetyl phosphate (trade name Amphisol® K). An example of a suitable acylglutamate is sodium stearoyl glutamate (trade name e.g. Eumulgin® SG). A further example of a suitable anionic surfactant is sodium lauryl glucose carboxylate (trade name Plantapon® LGC).

Cationic surfactants which can be used are in particular quaternary ammonium compounds. In one or more embodiments, the surfactant comprises ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Suitable pseudo cationic surfactants are, for example, stearylaminopropyldimethylamine (commercially available under the trade name Dehyquart® S18 or Incromine® SB or TegoAmide® S18). Furthermore, the very readily biodegradable quaternary ester compounds, such as, for example, the dialkylammonium methosulfates and methylhydroxyalkyldialkoyl-oxyalkylammonium methosulfates sold under the trade name Stepantex® and the corresponding products of the Dehyquart® series, can be used as cationic surfactants. The term "esterquats" is generally understood as meaning quaternized fatty acid triethanolamine ester salts. They can impart a particular soft feel to the preparations according to the invention. These are known substances which are prepared by the relevant methods of organic chemistry. Further cationic surfactants which can be used according to one or more embodiments of the invention are the quaternized protein hydrolysates. Suitable cationic surfactants are, for example, Dipalmitoylethyl Hydroxyethylmonium Methosulfate (trade name Dehyquart® C4046), Distearoylethyl Hydroxyethylmonium Methosulfate (trade name Dehyquart® F75), Dicocoylethyl Hydroxyethylmonium Methosulfate (trade name Dehyquart® L80), Behentrimonium Chloride (trade name Varisoft® BT), Distearyldimonium Chloride (trade name Varisoft® TA 100), Palmitamidopropyltrimonium Chloride (trade name Varisoft® PATC).

Wax Component b-2)

In one embodiment of the invention, the preparations according to one or more embodiments of the invention comprise at least one wax component. The preparations according to one or more embodiments of the invention comprise the wax component(s) in an amount of from 0 to 40% by weight, in particular from 0 to 20% by weight, or more specifically 0.1 to 15% by weight and in particular 0.1 to 10% by weight, based on the total weight of the preparation.

The term wax is usually understood as meaning all natural or synthetically obtained substances and substance mixtures having the following properties: they are of solid to brittly hard consistency, coarse to finely crystalline, transparent to cloudy and melt above 30° C. without decomposition. They are already of low viscosity a little above the melting point and are not thread-drawing and exhibit a highly temperature-dependent consistency and solubility. According to various embodiments of the invention, it is possible to use one wax component or a mixture of wax components which melt at 30° C. or above.

According to various embodiments of the invention, fats and fat-like substances with a wax-like consistency can also be used as waxes provided they have the required melting point. These include inter alia fats (triglycerides), mono- and diglycerides, natural and synthetic waxes, fatty and wax alcohols, fatty acids, esters of fatty alcohols and fatty acids, and fatty acid amides or any desired mixtures of these substances.

Fats are understood as meaning triacylglycerols, i.e. the triple esters of fatty acids with glycerol. In some embodiments, they comprise saturated, unsaturated and unsubstituted fatty acid radicals. These may also be mixed esters, i.e. triple esters of glycerol with various fatty acids. So-called hydrogenated fats and oils which are obtained by partial hydrogenation can be used according to one or more embodiments of the invention and are particularly well suited as consistency regulators. Plant hydrogenated fats and oils are may be used, e.g. hydrogenated castor oil, peanut oil, soya oil, rapeseed oil, colza seed oil, cotton seed oil, soya oil, sunflower oil, palm oil, palm kernel oil, linseed oil, almond oil, corn oil, olive oil, sesame oil, cocoa butter, shea butter and coconut fat.

The triple esters of glycerol with C12-C60-fatty acids and in particular C12-C36-fatty acids are inter alia suitable. These include hydrogenated castor oil, a triple ester of glycerol and a hydroxystearic acid, which is commercially available for example under the name Cutina HR. Likewise suitable are glycerol tristearate, glycerol tribehenate (e.g. Syncrowax HRC), glycerol tripalmitate or the triglyceride mixtures known under the name Syncrowax HGLC, with the proviso that the melting point of the wax component or of the mixture is 30° C. or above.

According to one or more embodiments of the invention, in particular mono- and diglycerides or mixtures of these partial glycerides can be used as wax components. The glyceride mixtures which can be used according to one or more embodiments of the invention include the products Novata AB and Novata B (mixture of C12-C18-mono-, di- and triglycerides) and also Cutina® HVG (Hydrogenated Vegetable Glycerides) or Cutina® GMS (glyceryl stearate) marketed by Cognis Deutschland GmbH & Co. KG.

The fatty alcohols which can be used according to one or more embodiments of the invention as wax component include the C12-C50-fatty alcohols. The fatty alcohols can be obtained from natural fats, oils and waxes, such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to one or more embodiments of the invention, saturated unbranched fatty alcohols are used. However, unsaturated, branched or unbranched fatty alcohols can also be used according to one or more embodiments of the invention as wax component provided they have the required melting point. According to various embodiments of the invention, it is also possible to use fatty alcohol segments, as are produced during the reduction of naturally occurring fats and oils such as e.g. beef tallow, peanut oil, coltsa oil, cotton oil, soya oil, sunflower oil, palm kernel oil, linseed oil, castor oil, corn oil, rapeseed oil, sesame oil, cocoa butter and cocoa fat. However, it is also possible to use synthetic alcohols, e.g. the linear, even-numbered fatty alcohols of the Ziegler synthesis (alfols) or the sometimes branched alcohols from the oxo synthesis (dobanols). According to one or more embodiments of the invention, C14-C22-fatty alcohols are suitable, which are marketed for example by Cognis Deutschland GmbH under the name Lanette 16 (C16-alcohol), Lanette 14 (C14-alcohol), Lanette O (C16/C18-alcohol) and Lanette 22 (C18/C22-alcohol). In some embodiments, fatty alcohols give the preparations a drier skin feel than triglycerides and are therefore used over the latter.

Wax components which can be used are also C14-C40-fatty acids or mixtures thereof. These include, for example, myristic acid, pentadecanoic acid, palmitic acid, margaric acid, stearic acid, nonadecanoic acid, arachic acid, behenic acid, lignoceric acid, cerotic acid, melissic acid, erucic acid and elaeostearic acid, and also substituted fatty acids, such as e.g. 12-hydroxystearic acid, and the amides or monoethanolamides of the fatty acids, this list being exemplary and non-limiting in character.

According to one or more embodiments of the invention, it is possible to use for example natural plant waxes, such as candelilla wax, carnauba wax, japan wax, esparto grass wax, cork wax, guaruma wax, ricegerm oil wax, sugarcane wax, ouricury wax, montan wax, sunflower wax, fruit waxes such as orange waxes, lemon waxes, grapefruit wax, bayberry wax and animal waxes, such as e.g. beeswax, schellack wax, spermaceti, wool wax and uropygial grease. Within the context of the invention, it may be advantageous to use hydrogenated waxes. The natural waxes which can be used according to one or more embodiments of the invention also include the mineral waxes, such as e.g. ceresin and ozokerite or the petrochemical waxes, such as e.g. petrolatum, paraffin waxes and microwaxes. Wax components which can be used are also chemically modified waxes, in particular the hard waxes, such as e.g. montan ester waxes, sasol waxes and hydrogenated jojoba waxes. The synthetic waxes which can be used according to one or more embodiments of the invention include, for example, wax-like polyalkylene waxes and polyethylene glycol waxes. In some embodiments, plant waxes are utilizd according to one or more embodiments of the invention.

The wax component can likewise be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (e.g. 12-hydroxystearic acid) and saturated and/or unsaturated, branched and/or unbranched alcohols, and also from the group of the lactides of long-chain hydroxycarboxylic acids. Examples of such esters are the C16-C40-alkyl stearates, C20-C40-alkyl stearates (e.g. Kesterwachs K82H), C20-C40-dialkyl esters of dimer acids, C18-C38-alkyl hydroxystearoylstearates or C20-C40-alkyl erucates. It is also possible to use C30-C50-alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate.

Polymers b-3)

In one embodiment of the invention, the preparations according to one or more embodiments of the invention comprise at least one polymer. The preparations according to one or more embodiments of the invention comprise the polymer(s) in an amount of from 0 to 20% by weight, or 0.05 to 18% by weight, or 0.05 to 15% by weight, or 0.05 to 10% by weight, in particular 0.1 to 1% by weight, based on the total weight of the preparations. In a specific embodiment of the invention, the preparations according to one or more embodiments of the invention comprise the polymer/polymers in an amount of from 0.1 to 5% by weight, in particular 0.1 to 3% by weight, in particular 0.1 to 2% by weight, based on the total weight of the preparation.

Suitable cationic polymers are, for example, cationic cellulose derivatives, such as e.g. a quaternized hydroxyethylcellulose, which is available under the name Polymer JR 400° from Amerchol, cationic starch, copolymers of diallylammonium salts and acrylamides, quaternized vinylpyrrolidone/vinylimidazole polymers, such as e.g. Luviquat® (BASF), condensation products of polyglycols and amines, quaternized collagen polypeptides, such as, for example, lauryldimonium hydroxypropyl hydrolyzed collagen (Lamequat® L/Grünau), quaternized wheat polypeptides, polyethyleneimine, cationic silicone polymers, such as e.g. amidomethicones, copolymers of adipic acid and dimethylaminohydroxypropyldiethylene-triamine (Cartaretine®/Sandoz), copolymers of acrylic acid with dimethyldiallylammonium chloride (Merquat® 550/Chemviron), polyaminopolyamides, cationic chitin derivatives such as, for example, quaternized chitosan, optionally in microcrystalline distribution, condensation products of dihaloalkylene, such as e.g. dibromobutane with bisdialkylamines, such as e.g. bis-dimethylamino-1,3-propane, cationic guar gum, such as e.g. Jaguar® CBS, Jaguar® C-17, Jaguar® C-16 from Celanese, quaternized ammonium salt polymers, such as e.g. Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked and polyol-crosslinked polyacrylic acids, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers, and optionally derivatized cellulose ethers and silicones.

Particularly suitable anionic polymers are those with the INCI name Carbomer, such as e.g. the Carbopol grades 980, 980, 981, 1382, 2984, 5984, and the products available under the trade names Rheocare® C plus and Rheocare® 400. Furthermore suitable anionic polymers are those with the INCI name Acrylates/C10-30 Alkyl Acrylate Crosspolymer (trade name e.g. Pemulen® TR, Pemulen® TR 2, Carbopol® Ultrez), Acrylates Copolymer (trade name e.g. Rheocare TTA, TTN, TTN-2), Acrylamide/Sodium Acrylate Copolymer (trade name e.g. Cosmedia® ATC), Sodium Polyacrylate (trade name e.g. Cosmedia® ATH, Cosmedia® SP), Polyacrylamides (trade name e.g. Sepigel® 305 or Sepigel® 501). In one or more embodiments, the anionic polymers are polyacrylic acid homopolymers and copolymers.

Furthermore suitable polymers are silicone elastomer gums, such as e.g. silicone elastomer mixtures, such as e.g. mixtures with the INCI names Cyclopentasiloxane (and) Dimethiconol (and) Dimethicone Crosspolymer (trade name Dow Corning® DC 9027), mixtures with the INCI name Isodecyl Neopentanoate (and) Dimethicone/bis-isobutyl PPG-20 Crosspolymer (trade name Dow Corning® DC EL 8051 IN), mixtures with the INCI name Dimethicone/Vinyl Dimethicone Crosspolymer (and) C12-14 Pareth-12) (trade name Dow Corning® DC 9509), and mixtures with the INCI name Dimethicone/Vinyl Dimethicone Crosspolymer (and) Silica (trade name Dow Corning® DC 9701 Cosmetic Powder).

Suitable polymers are likewise polysaccharides, in particular xanthan gum, guar gum, agar agar, alginates and tyloses, and also tara gum, carrageenan, sclerotium gum and natural cellulose.

Further Oil Bodies b-4)

Bodycare compositions, such as creams, body oils, lotions and milks, usually comprise a series of further oil bodies and emollients which contribute to further optimizing the sensory properties. The oil bodies (compounds according to one or more embodiments of the invention plus further oil bodies) are usually present in a total amount of 0.1-80, or 0.5 to 70, or 1 to 60, or 1 to 50% by weight, or 1 to 40% by weight, or 5-25% by weight and more specifically 5-15% by weight. The other oil bodies are usually present in an amount of from 0.1 to 40% by weight.

Suitable further oil bodies are, for example, Guerbet alcohols based on fatty alcohols having 6 to 18, and in further embodiments 8 to 10, carbon atoms, and also esters such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkylhydroxycarboxylic acids with linear or branched $C_6$-$C_{22}$-fatty alcohols, in particular dioctyl malate, esters of linear and/or branched fatty acids with polyhydric alcohols (such as e.g. propylene glycol, dimerdiol or trimertriol), triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with polyols having 2 to 10 carbon atoms and 2 to 6 hydroxyl groups, plant oils, branched primary alcohols, substituted cyclohexanes, linear and branched $C_6$-$C_{22}$-fatty alcohol carbonates, such as e.g. Dicaprylyl Carbonate (Cetiol® CC), Guerbet carbonates based on fatty alcohols having 6 to 18, or 8 to 10 carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as e.g. dicaprylyl ether (Cetiol® OE), ring-opening products of epoxidized fatty acid esters with polyols and hydrocarbons or mixtures thereof. Also suitable are esters of 2-propylheptanol with n-octanoic acid, such as e.g. commercially available under the trade name Cetiol®SenSoft (Cognis GmbH). Also suitable are hydrocarbons, such as for example undecane and tridecane. Also suitable are alkanes, such as e.g. the mixtures with the INCI name Coconut/Palm/Palm Kernel Oil Alkanes (trade name Vegelight 1214 from Biosynthesis).

Surprisingly, it has been found that the compounds according to one or more embodiments of the invention are suitable in particular for solubilizing oil-soluble crystalline UV photoprotective filters.

One subject matter of the invention relates to preparations comprising at least one compound according to claim 1 and at least one UV photoprotective filter, and in further embodiments, an oil-soluble UV photoprotective filter.

According to one or more embodiments of the invention, suitable UV photoprotective filters are organic substances (photoprotective filters) that are liquid or crystalline at room temperature and which are able to absorb ultraviolet radiation and release the absorbed energy again in the form of longer-wave radiation, e.g. heat. UV filters can be oil-soluble or water-soluble. Typical oil-soluble UV-B filters or broad spectrum UV A/B filters to be mentioned are e.g.:

3-benzylidenecamphor or 3-benzylidenenorcamphor (Mexoryl SDS 20) and derivatives thereof, e.g. 3-(4-methylbenzylidene)camphor, as described in EP 0693471 B1

3-(4'-trimethylammonium)benzylidenebornan-2-one methylsulfate (Mexoryl SO)

3,3'-(1,4-phenylenedimethine)bis(7,7-dimethyl-2-oxobicyclo[2.2.1]heptane-1-methanesulfonic acid) and salts (Mexoryl SX)

3-(4'-sulfo)benzylidenebornan-2-one and salts (Mexoryl SL)

polymer of N-{(2 and 4)[2-oxoborn-3-ylidene)methyl}benzyl]acrylamide (Mexoryl SW)

2-(2H-benzotriazol-2-yl)-4-methyl-6-(2-methyl-3-(1,3,3,3-tetramethyl-1-(trimethylsilyloxy)disiloxanyl)propyl) phenol (Mexoryl SL)

4-aminobenzoic acid derivatives, specifically 2-ethylhexyl 4-(dimethylamino)benzoate, 2-octyl 4-(dimethylamino)benzoate and amyl 4-(dimethylamino)benzoate;

esters of cinnamic acid, specifically 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, specifically 2-ethylhexyl salicylate, 4-isopropylbenzyl salicylate, homomethyl salicylate;

derivatives of benzophenone, specifically 2-hydroxy-4-methoxybenzophenone, 2-hydroxy-4-methoxy-4'-methylbenzophenone, 2,2'-dihydroxy-4-methoxybenzophenone;

esters of benzalmalonic acid, specifically di-2-ethylhexyl 4-methoxybenzmalonate;

triazine derivatives, such as e.g. 2,4,6-trianilino(p-carbo-2'-ethyl-1'-hexyloxy)-1,3,5-triazine and 2,4,6-tris[p-(2-ethylhexyloxycarbonyl)anilino]-1,3,5-triazine (Uvinul T 150) as described in EP 0818450 A1 or bis(2-ethylhexyl) 4,4'-[(6-[4-((1,1-dimethylethyl)aminocarbonyl)phenylamino]-1,3,5-triazine-2,4-diyl)diimino]bisbenzoate (Uvasorb® HEB);

2,2-(methylenebis(6-(2H-benzotriazol-2-yl)-4-(1,1,3,3-tetramethylbutyl)phenol) (Tinosorb M);

2,4-bis[4-(2-ethylhexyloxy)-2-hydroxyphenyl]-6-(4-methoxyphenyl)-1,3,5-triazine (Tinosorb S);

propane-1,3-diones, such as e.g. 1-(4-tert-butylphenyl)-3-(4'-methoxyphenyl)propane-1,3-dione;

ketotricyclo(5.2.1.0)decane derivatives, as described in EP 0694521 B1;

dimethicodiethylbenzalmalonates (Parsol SLX).

Suitable water-soluble UV filters are:

2-phenylbenzimidazole-5-sulfonic acid and the alkali metal, alkaline earth metal, ammonium, alkyl ammonium, alkanol ammonium and glucammonium salts thereof;

2,2-((1,4-phenylene)bis(1H-benzimidazole-4,6-disulfonic acid, monosodium salt) (Neo Heliopan AP)

sulfonic acid derivatives of benzophenones, specifically 2-hydroxy-4-methoxybenzophenone-5-sulfonic acid and its salts;

sulfonic acid derivatives of 3-benzylidenecamphor, such as e.g. 4-(2-oxo-3-bornylidenemethyl)benzenesulfonic acid and 2-methyl-5-(2-oxo-3-bornylidene)sulfonic acid and salts thereof.

In a one or more embodiments of the invention, the preparations comprise at least one oil-soluble UV photoprotective filter and at least one water-soluble UV photoprotective filter.

Suitable typical UV-A filters are in particular derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and also enamine compounds, as described in DE 19712033 A1 (BASF), and also benzoic acid, 2-[4-(diethylamino)-2-hydroxybenzoyl]-, Hexyl Ester (Uvinul® A plus).

The UV-A and UV-B filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, specifically 2-ethylhexyl 4-methoxycinnamate and/or propyl 4-methoxycinnamate and/or isoamyl 4-methoxycinnamate. Combinations of this type are advantageously combined with water-soluble filters such as e.g. 2-phenylbenzimidazole-5-sulfonic acid and the alkali metal, alkaline earth metal, ammonium, alkyl ammonium, alkanol ammonium and glucammonium salts thereof.

The preparations according to one or more embodiments of the invention can also comprise insoluble photoprotective pigments, namely finely disperse metal oxides and/or salts. Examples of suitable metal oxides are in particular zinc oxide and titanium dioxide and also oxides of iron, zirconium, silicon, manganese, aluminum and cerium, and mixtures thereof. Salts which can be used are silicates (talc), barium sulfate or zinc stearate. The oxides and salts are used in the form of the pigments for skincare and skin-protecting emulsions and also for decorative cosmetics. The particles should have an average diameter of less than 100 nm, specifically between 5 and 50 nm and in particular between 15 and 30 nm. They can have a spherical form, although it is also possible to use particles which have an ellipsoidal form or a form which deviates in some other way from the spherical shape. The pigments can also be present in surface-treated form, i.e. hydrophilicized or hydrophobicized. Typical examples thereof are coated titanium dioxides, such as e.g. titanium dioxide T 805 (Degussa) or Eusolex® T, Eusolex® T-2000, Eusolex® T-Aqua, Eusolex® AVO, Eusolex® T-ECO, Eusolex® T-OLEO and Eusolex® T-S (Merck). Typical examples thereof are zinc oxides, such as e.g. zinc oxide neutral, zinc oxide NDM (Symrise) or Z-Cote® (BASF) or SUNZnO-AS and SUNZnO-NAS (Sunjun Chemical Co. Ltd.). Suitable hydrophobic coatings here are primarily silicones and specifically trialkoxyoctylsilanes or simethicones. In embodiments related to sunscreen compositions, so-called micropigments or nanopigments may be used. In further embodiments, micronized zinc oxide is used.

As well as the two aforementioned groups of primary photoprotective substances, it is also possible to use secondary photoprotective agents of the antioxidant type, which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. -carotene, -carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO4), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to one or more embodiments of the invention of these specified active ingredients.

In a one or more embodiments of the invention, the preparations comprise at least one UV photoprotective filter selected from the group consisting of 4-methylbenzylidenecamphor, benzophenone-3, butylmethoxydibenzoyl methane, bis-ethylhexyloxyphenol methoxyphenyl triazine, methylene bis-benzotriazolyl tetramethylbutylphenol, diethylhexyl butamidotriazone, ethylhexyl triazone and diethylamino hydroxybenzoyl hexyl benzoate, 3-(4'-trimethylammonium)benzylidenebornan-2-one methylsulfate, 3,3'-(1,4-phenylene-dimethine)bis(7,7-dimethyl-2-oxobicyclo[2.2.1]heptane-1-methanesulfonic acid) and its salts, 3-(4'sulfo)benzylidenebornan-2-one and its salts, polymer of N-{(2 and 4)-[2-oxoborn-3-ylidene)methyl}benzyl]acrylamide, 2-(2H-benzotriazol-2-yl)-4-methyl-6-(2-methyl-3-(1, 3,3,3-tetramethyl-1-(trimethylsilyloxy)disiloxanyl)propyl) phenol, dimethicodiethyl benzal-malonate and their mixtures.

These UV photoprotective filters are commercially available, for example, under the following trade names:

NeoHeliopan® MB C (INCI: 4-methylbenzylidene camphor; manufacturer: Symrise); NeoHeliopan® BB (INCI: benzophenone-3, manufacturer: Symrise); Parsol® 1789 (INCI: butyl methoxydibenzoylmethane, manufacturer: Hoffmann La Roche (Givaudan); Tinosorb® S (INCI: bis-ethylhexyloxyphenol methoxyphenyl triazine); Tinosorb® M (INCI: methylene bis-benzotriazolyl tetramethylbutylphenol): manufacturer: Ciba Specialty Chemicals Corporation; Uvasorb® HEB (INCI: diethylhexyl butamidotriazone, manufacturer: 3V Inc.), Unvinul® T 150 (INCI: ethylhexyl triazone, manufacturer: BASF AG); Uvinul® A plus (INCI: diethylamino hydroxybenzoyl hexyl benzoate: manufacturer: BASF AG; Mexoryl® SO: 3-(4'-trimethylammonium)benzylidenebornan-2-one methylsulfate, INCI: camphor benzalkonium methosulfate; Mexoryl® SX: 3,3'-(1,4-phenylene-dimethine)bis(7,7-dimethyl-2-oxobicyclo[2.2.1]heptane-1-methanesulfonic acid), CTFA: INCI terephthalylidene dicamphor sulfonic acid; Mexory® SL: 3-(4'-sulfo)benzylidenebornan-2-one, INCI benzylidene camphor sulfonic acid; Mexoryl® SW: polymer of N-{(2 and 4)-[2-oxoborn-3-ylidene)methyl}benzyl]acrylamide, INCI polyacrylamidomethyl benzylidene camphor; Mexoryl® SL: 2-(2H-benzotriazol-2-yl)-4-methyl-6-(2-methyl-3-(1,3,3,3-tetramethyl-1-(trimethylsilyloxy)disiloxanyl)propyl)phenol; INCI: DROMETRIZOLE TRISILOXANE; Parsol® SLX: dimethicodiethylbenzalmalonate, INCI polysilicone-15.

The preparations according to one or more embodiments of the invention can comprise the UV photoprotective filters in amounts of from 0.5 to 30% by weight, specifically 2.5 to 20% by weight, particularly specifically 5-15% by weight—based on the preparation.

Further Ingredients

Suitable thickeners are, for example, Aerosil grades (hydrophilic silicas), carboxymethylcellulose and hydroxyethyl- and hydroxypropylcellulose, polyvinyl alcohol, polyvinylpyrrolidone and bentonite such as e.g. Bentone® Gel VS-5PC (Rheox). A suitable thickener is for example the product with the INCI name Dicaprylyl Carbonate, Stearalkonium Hectorite and Propylene Carbonate available under the trade names Cosmedia® Gel CC. Biogenic active ingredients are to be understood as meaning, for example, tocopherol, tocopherol acetate, tocopherol palmitate, ascorbic acid, (deoxy)ribonucleic acid and a fragmentation product thereof, β-glucans, retinol, bisabolol, allantoin, phytantriol, panthenol, AHA acids, amino acids, ceramides, pseudoceramides, essential oils, plant extracts, such as e.g. prune extract, bambara nut extract and vitamin complexes. Deodorizing active ingredients/antiperspirants counteract, mask or eliminate body odors. Body odors are formed as a result of the action of skin bacteria on apocrine perspiration, during which unpleasant smelling degradation products are formed. Accordingly, antimicrobial agents, enzyme inhibitors, odor absorbers or odor maskers, inter alia, are suitable as deodorizing active ingredients. Suitable insect repellents are, for example, N,N-diethyl-m-toluamide, 1,2-pentanediol or ethyl 3-(N-n-butyl-N-acetylamino)propionate), which is sold under the name Insect Repellent® 3535 by Merck KGaA, and also butylacetylaminopropionate. A suitable self-tanning agent is dihydroxyacetone or erythrulose. Suitable tyrosine inhibitors, which prevent the formation of melanin and are used in depigmentation compositions, are, for example, arbutin, ferulic acid, kojic acid, cumaric acid and ascorbic acid (vitamin C). Suitable preservatives are, for example, phenoxyethanol, formaldehyde solutions, parabens, pentanediol, chlorphenesin, caprylyl glycol, ethylhexylglycerols or sorbic acid, and also the silver complexes known under the name Surfacine® and the other substance classes listed in annex 6, part A and B of the Cosmetics Ordinance. Perfume oils which may be mentioned are mixtures of natural and synthetic fragrances. Natural fragrances are extracts from flowers, stems and leaves, fruits, fruit peels, roots, woods, herbs and grasses, needles and branches, resins and balsams. Also suitable are animal raw materials, such as, for example, civet and castoreum, and also synthetic fragrance compounds of the ester, ether, aldehyde, ketone, alcohol and hydrocarbon types. Suitable pearlescent waxes or pearlescent compounds, particularly for use in surface-active formulations, are, for example: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in total at least 24 carbon atoms, specifically laurone and distearyl ether; stearyl citrate, cyclodextrin, fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof. Superfatting agents which can be used are substances such as, for example, lanolin and lecithin, and also polyethoxylated or acylated lanolin and lecithin derivatives, polyol fatty acid esters, monoglycerides and fatty acid alkanolamides, the latter simultaneously serving as foam stabilizers. A suitable superfatting agent is, for example, the mixture of cocoglucosides and glyceryl oleate (commercially available as Lamesoft® PO65 from Cognis GmbH).

Suitable fillers are substances which, for example, improve the sensory or cosmetic properties of a preparation and which, for example, produce or boost a velvety or silky feel (so-called skin sensory modifier). Suitable fillers are starch and starch derivatives (such as e.g. tapioca starch, aluminum starch octenyl succinate, sodium octenyl succinate, distarch phosphate), pigments which do not serve primarily as UV filters or dyes (such as e.g. boron nitride) and/or Aerosil® (CAS No. 7631-86-9), and/or talc, and also for example polymethyl methacrylate (e.g. Cosmedia® PMMA V8/V12), silica (e.g. Cosmedia® SILC), stearalkonium hectorite (as present in the commercially available product Cosmedia® Gel CC), and also HDI/trimethylol hexyllactone crosspolymer (as present in the commercially available product Cosmedia® CUSHION).

Stabilizers which can be used are metal salts of fatty acids, such as e.g. magnesium, aluminum and/or zinc stearate or ricinoleate. To improve the flow behavior, also hydrotropes, such as, for example, ethanol isopropyl alcohol, or polyols, can be used. Polyols which are suitable here have specifically 2 to 15 carbon atoms and at least two hydroxyl groups. The polyols can also contain further functional groups, in particular amino groups, and/or be modified with nitrogen.

The preparations according to the invention, and also the compounds described herein are suitable in particular in cosmetic and/or pharmaceutical preparations for the wetting or impregnation or coating of utility wipes and hygiene wipes which are used for cleaning the body and/or for bodycare.

Utility wipes and hygiene wipes which may be mentioned by way of example are: tissues, papers, wipes, nonwoven products, sponges, puffs, plasters and bandages which are used in the field of hygiene and care. These may be wet wipes for baby hygiene and babycare, cleansing wipes, face cleansing wipes, skincare wipes, care wipes with active ingredients to combat skin aging, wipes with sunscreen formulations and insect repellents, and also wipes for decorative cosmetics or for after-sun treatment, toilet wet wipes, antiperspirant wipes, diapers, pocket tissues, wet wipes, hygiene products, and self-tanning wipes.

EXAMPLES (1) Preparation Examples

Synthesis of the Guerbet Alcohols in the Laboratory

The syntheses below were carried out with the following specifications:

Lanette O—Cetylstearyl alcohol with chain distribution C16 of 45-55% and C18 of 45-55%

Lorol—"Lorol technical-grade", C12-18 fatty alcohol with the following chain distribution:
C12 48-58%
C14 18-24%
C16 8-12%
C18 11-15%

A) Example Synthesis

Lanette O/Lorol 70:30

2700 g of Lanette O were mixed with 1160 g of Lorol and to the melt were added 0.08 g of zinc oxide and, in portions, 70 g of 50% strength aqueous sodium hydroxide solution.

The mixture was heated to firstly 220° C. under partial reflux, at which the alcohols were retained, but the water of reaction was able to escape. After a few hours, the temperature was increased stepwise to 250° C.

As soon as the target conversion had been reached, the mixture was washed once with water and the remaining amount of alkali was neutralized with lactic acid, dried in vacuo and filtered with filtration aid through a deep bed filter.

B) Example Synthesis

Lanette O/Lorol 65:35

845 g of Lanette O were mixed with 455 g of Lorol and to the melt were added 0.025 g of zinc oxide and, in portions, 22 g of 50% strength aqueous potassium hydroxide solution.

The mixture was heated to firstly 220° C. under partial reflux, at which the alcohols were retained, but the water of reaction was able to escape. After a few hours, the temperature was increased stepwise to 250° C.

As soon as the target conversion had been reached, the mixture was washed once with water and the remaining amount of alkali was neutralized with lactic acid, dried in vacuo and filtered with filtration aid through a deep bed filter.

C) Example Synthesis

Lanette O/Lorol 60:40

300 g of Lanette O were mixed with 200 g of Lorol and to the melt were added 0.01 g of zinc oxide and, in portions, 10 g of 50% strength aqueous potassium hydroxide solution.

The mixture was heated to firstly 220° C. under partial reflux, at which the alcohols were retained, but the water of reaction was able to escape. After a few hours, the temperature was increased stepwise to 250° C.

As soon as the target conversion had been reached, the mixture was washed once with water and the remaining amount of alkali was neutralized with lactic acid, dried in vacuo and filtered with filtration aid through a deep bed filter.

D) Example Synthesis

Lanette O/Ocenol 95:5

1235 g of Lanette O were mixed with 65 g of HD Ocenol 60/65 and to the melt were added 0.025 g of zinc oxide and, in portions, 22 g of 50% strength aqueous potassium hydroxide solution.

The mixture was heated to firstly 220° C. under partial reflux, at which the alcohols were retained, but the water of reaction was able to escape. After a few hours, the temperature was increased stepwise to 250° C.

As soon as the target conversion had been reached, the mixture was washed once with water and the remaining amount of alkali was neutralized with lactic acid, dried in vacuo and filtered with filtration aid through a deep bed filter.

E) Example Synthesis

Lanette O/Lorol/Hexanediol 62.5:32.5:5

312.5 g of Lanette O were mixed with 162.5 g of Lorol and 25 g of hexane-1,6-diol and to the melt were added 0.08 g of zinc oxide and, in portions, 80 g of 50% strength aqueous potassium hydroxide solution.

The mixture was heated to firstly 220° C. under partial reflux, at which the alcohols were retained, but the water of reaction was able to escape. After a few hours, the temperature was increased stepwise to 250° C.

As soon as the target conversion had been reached, the mixture was washed once with water and the remaining amount of alkali was neutralized with lactic acid, dried in vacuo and filtered with filtration aid through a deep bed filter.

(2) Formulation and Sensorics

A) The application properties of the Guerbet alcohols were investigated in a cosmetic formulation with 1% by weight of Cosmedia® SP (sodium polyacrylate), 10% by weight of Cetiol® LC (cococaprylate/caprate) and 3% by weight of glycerol. The use concentration of Guerbet alcohols and/or petroleum jelly was 6% by weight in each case.

TABLE 2.1

| Formulation: | | | | |
|---|---|---|---|---|
| | C | 1 | 2 | 3 |
| COSMEDIA ® SP (sodium polyacrylate) | 1.0 | 1.0 | 1.0 | 1.0 |
| CETIOL ® LC (coc-caprylate/caprate) | 10.0 | 10.0 | 10.0 | 10.0 |
| petroleum jelly, white (Sigma Aldrich) | 6.0 | — | — | — |
| Guerbet alcohol mixture A (70:30) | — | 6.0 | — | — |
| Guerbet alcohol mixture B (65:35) | | | 6.0 | |
| Guerbet alcohol mixture E | | | | 6.0 |
| Glycerol | 3.0 | 3.0 | 3.0 | 3.0 |
| Water, demin. | 79.9 | 79.9 | 79.9 | 79.9 |
| Euxyl K 100 (preservative) | 0.1 | 0.1 | 0.1 | 0.1 |
| pH | 6.1 | 6.4 | 6.0 | 6.0 |
| Viscosity (Brookfield, RVF, 23° C., Spindel TE, 4 rpm, with Helipath) mPa * s | 162500 | 125000 | 162500 | 125000 |

Sensorics Compared to Petroleum Jelly in a Cosmetic Formulation:

The sensorics of the formulation were evaluated by five test persons according to defined criteria. Petroleum jelly represents the standard in the comparison (+ describes the judgement of one test person). The formulation with the Guerbet alcohol mixture B (63:35) exhibits comparable sensory properties to the petroleum jelly formulation. In particular, compared to the standard, it absorbs somewhat more rapidly into the skin and is perceived to be less oily and wax-like.

TABLE 2.2

| Results of the sensory investigation | | | |
|---|---|---|---|
| | − | Standard | + |
| Spreading (low) | | +++++ | Spreading (high) |
| Absorption 1 min (slow) | | +++ | ++ Absorption 1 min (rapid) |
| Absorption 3 min (slow) | | ++++ | + Absorption 3 min (rapid) |
| Residues (many) | | ++++ | + Residues (few) |
| Stickiness (considerable) | | ++++ | + Stickiness (slight) |
| Oiliness (considerable) | | +++ | ++ Oiliness (slight) |
| Waxiness (considerable) | + | ++ | ++ Waxiness (slight) |
| Velvetiness (slight) | | ++++ | + Velvetiness (pronounced) |
| Silkiness (slight) | | +++++ | Silkiness (pronounced) |
| Powder feel (slight) | | +++++ | Powder feel (pronounced) |
| Softness (slight) | + | ++ | ++ Softness (pronounced) |
| Smoothness (slight) | + | +++ | + Smoothness (pronounced) |
| Care feel (slight) | + | ++ | ++ Care feel (pronounced) |
| Acceptance (slight) | | ++++ | + Acceptance (high) |

(3) Use in Surfactant Systems

The application properties of the Guerbet alcohols were investigated in a surface-active formulation comprising 16.1% Texapon® N70 (sodium laureth sulfate 2EO), 11.1% Dehyton® PK45 (cocamidopropylbetaine), 2.15% Comperlan® CMEA (Cocamide MEA), 4% sunflower oil, 4% Edenor® C12 (lauric acid), 0.2% Dehyquart® GUAR N (guar hydroxypropyltrimonium chloride), 0.2% EDTA BD, 0.5% glycerol, 0.5% sodium benzoate and 1.2% citric acid. The use concentration of Guerbet alcohols and/or petroleum jelly was 4% by weight in each case.

TABLE 3.1

| Formulation: | | |
|---|---|---|
| | 4 | 5 |
| TEXAPON ® N70 | 16.1 | 16.1 |
| DEHYTONL ® PK45 | 11.1 | 11.1 |
| COMPERLAN ® CMEA | 2.15 | 2.15 |
| Sunflower oil | 4.0 | 4.0 |
| Edenor C 12 | 4.0 | 4.0 |
| Petroleum jelly, white (Sigma Aldrich) | — | 4.0 |
| Guerbet alcohol mixture A (65:35) | 4.0 | — |
| DEHYQUART ® GUAR N | 0.2 | 0.2 |
| EDTA BD | 0.2 | 0.2 |
| Glycerol | 0.5 | 0.5 |
| Sodium benzoate | 0.5 | 0.5 |
| Water, demin. | 56.05 | 56.55 |
| Citric acid (50%) | 1.2 | 0.7 |
| pH | 4.6 | 4.9 |
| Viscosity (Brookfield, RVF, 23° C., Spindel 5, 10 rpm) mPa * s | 13400 | 14400 |

Foaming Properties

The foaming properties were determined in a Sita Rotorfoam measuring device in a 1% strength by weight solution at 15° German hardness at 30° C. The foaming behavior of the Guerbet formulation, in particular the initial foaming after ca. 30 seconds, is comparable to the formulation with petroleum jelly. In the further course of the measurement, the test formulation based on Guerbet develops a larger amount of foam than the petroleum jelly formulation. The investigated new Guerbet alcohols therefore offer comparable or better application properties than petroleum jelly.

TABLE 3.2

Foaming properties

| Time [s] | Foam height in ml | |
|---|---|---|
| | 4 with Guerbet alcohol mixture A | with Petroleum jelly |
| 30 | 138 | 126 |
| 60 | 155 | 134 |
| 90 | 190 | 139 |
| 120 | 208 | 150 |
| 150 | 218 | 154 |
| 180 | 229 | 156 |
| 210 | 241 | 149 |
| 240 | 242 | 150 |
| 270 | 253 | 150 |
| 300 | 261 | 126 |

(4) Occlusivity

The occlusivity of the Guerbet alcohols was determined by determining the TEWL (transepidermal water loss).

The occlusive effect was determined via the reduction in the water permeability of the skin using an evaporimeter process. For this, the water vapor gradient was measured above the oil-treated or untreated skin of the forearm using two measuring probes in a climatically controlled environment, and the water permeability of the skin was ascertained from this.

Petroleum jelly was used as a positive standard, and IPM was used as a negative standard. The samples are arranged below in terms of the occlusivity:

1. Petroleum jelly—pronounced to strongly occlusive
2. Guerbet alcohol mixture B—moderately to strongly occlusive
3. Guerbet alcohol mixture D—moderately to strongly occlusive
4. IPM-CE92010016 pronounced to a little occlusive Both investigated Guerbet alcohols exhibit strongly occlusive properties and are therefore well suited as petroleum jelly substitute.

What is claimed is:

1. A Guerbet alcohol mixture obtainable by reacting:
   a) 55 to 70% by weight of cetylstearyl alcohol; with
   b) 5 to 40% by weight of fatty alcohols with a chain length of 8 to 22 carbon atoms; and
   c) 5% by weight of an aliphatic diol having at least 3 carbon atoms,
   with the proviso that the mixture has a melting range, measured by differential scanning calorimetry (DSC), between −20° C. and +70° C., where the width of the melting range comprises at least 30 temperature degrees and the maximum of the melting range is 35±15° C.

2. The Guerbet alcohol mixture of claim 1, wherein the Guerbet alcohol mixture has a melting range between −10° C. and +60° C., where the width of the melting range comprises at least 40 temperature degrees and the maximum of the melting range is 35±10° C.

3. The Guerbet alcohol mixture of claim 1, wherein the component a) consists of unbranched fatty alcohols with a chain distribution of
   C16 of 45-55%, and
   C18 of 45-55%.

4. The Guerbet alcohol mixture of claim 1, wherein the component b) consists essentially of fatty alcohols with a chain length of from 12 to 18 carbon atoms.

5. The Guerbet alcohol mixture of claim 1, wherein the component b) consists of unbranched, saturated fatty alcohols having the following chain distribution:
   C12 from 48-58% by weight
   C14 from 18-24% by weight
   C16 from 8-12% by weight
   C18 from 11-15% by weight.

6. The Guerbet alcohol mixture of claim 1, wherein component c) comprises hexanediol.

7. The Guerbet alcohol mixture of claim 1, wherein the Guerbet reaction is carried out at temperatures of from 200 to 260° C.

8. The Guerbet alcohol mixture of claim 1, wherein the Guerbet reaction is operated until 60-80% of the conversion of the starting alcohols has been achieved.

9. A cosmetic and/or pharmaceutical preparation comprising the Guerbet alcohol mixture of claim 1.

* * * * *